US008828692B2

(12) United States Patent
Hickey et al.

(10) Patent No.: US 8,828,692 B2
(45) Date of Patent: *Sep. 9, 2014

(54) MEMBRANE SUPPORTED BIOREACTOR FOR CONVERSION OF SYNGAS COMPONENTS TO LIQUID PRODUCTS (75) Inventors: Robert Hickey, Okemos, MI (US); Rathin Datta, Chicago, IL (US); Shih-Perng Tsai, Naperville, IL (US); Rahul Basu, Saint Charles, IL (US)

(73) Assignee: Coskata, Inc., Warrenville, IL (US)

( * ) Notice: Subject to any disclaimer, the term of this patent is extended or adjusted under 35 U.S.C. 154(b) by 584 days.

This patent is subject to a terminal disclaimer.

(21) Appl. No.: 13/101,535

(22) Filed: May 5, 2011

(65) Prior Publication Data
US 2011/0256597 A1    Oct. 20, 2011

Related U.S. Application Data (63) Continuation-in-part of application No. 11/972,454, filed on Jan. 10, 2008, now abandoned, which is a continuation-in-part of application No. 11/781,717, filed on Jul. 23, 2007, now abandoned.

(60) Provisional application No. 60/942,938, filed on Jun. 8, 2007.

(51) Int. Cl.
  C12P 7/54    (2006.01)
  C12M 1/00    (2006.01)
  C12M 1/12    (2006.01)
  C12P 7/04    (2006.01)
  C12M 1/34    (2006.01)

(52) U.S. Cl.
  CPC  *C12P 7/04* (2013.01); *C12M 23/58* (2013.01); *C12M 25/10* (2013.01); *C12M 21/12* (2013.01); Y02E 50/17 (2013.01); *C12M 29/16* (2013.01); *C12M 41/28* (2013.01)
  USPC ........................... 435/140; 435/141; 435/161

(58) Field of Classification Search
  CPC ...... C12M 23/58; C12M 25/10; C12M 21/12; C12M 29/16; C12M 41/28; C12P 7/04; Y02E 50/17
  USPC .......................................... 435/140, 141, 161
  See application file for complete search history.

(56) References Cited

U.S. PATENT DOCUMENTS

| 4,442,206 A * | 4/1984 | Michaels et al. ............. 435/71.1 |
| 8,309,348 B2 * | 11/2012 | Tsai et al. .................. 435/297.2 |
| 2003/0211585 A1 * | 11/2003 | Gaddy et al. .................. 435/161 |

* cited by examiner

Primary Examiner — Michael Marcheschi
Assistant Examiner — Jonathan Hurst (57) ABSTRACT Ethanol and other liquid products are produced by contacting syngas components such as CO or a mixture of $CO_2$ and $H_2$ with a surface of a membrane under anaerobic conditions and transferring these components into contact with a biofilm on the opposite side of the membrane. These steps provide a stable system for producing liquid products such as ethanol, butanol and other chemicals. The gas fed on the membrane's gas contact side transports through the membrane to form a biofilm of anaerobic microorganisms that converted the syngas to desired liquid products. The system can sustain production with a variety of microorganisms and membrane configurations.

21 Claims, 5 Drawing Sheets

MEMBRANE SUPPORTED BIOREACTOR FOR CONVERSION OF SYNGAS COMPONENTS TO LIQUID PRODUCTS

CROSS REFERENCE TO RELATED APPLICATIONS

This application is a continuation in part of U.S. application Ser. No. 11/972,454 filed Jan. 10, 2008 (now abandoned), which is a continuation in part of U.S. application Ser. No. 11/781,717 filed Jul. 23, 2007 (now abandoned), which is an application claiming benefit under 35 USC 119(c) of U.S. Provisional Patent Application Ser. No. 60/942,938 filed Jun. 8, 2007.

FIELD OF THE INVENTION

This invention relates to the biological conversion of CO and mixtures of $CO_2$ and $H_2$ to liquid products.

DETAILED DESCRIPTION

Background

Biofuels production for use as liquid motor fuels or for blending with conventional gasoline or diesel motor fuels is increasing worldwide. Such biofuels include, for example, ethanol and n-butanol. One of the major drivers for biofuels is their derivation from renewable resources by fermentation and bioprocess technology. Conventionally, biofuels are made from readily fermentable carbohydrates such as sugars and starches. For example, the two primary agricultural crops that are used for conventional bioethanol production are sugarcane (Brazil and other tropical countries) and corn or maize (U.S. and other temperate countries). The availability of agricultural feedstocks that provide readily fermentable carbohydrates is limited because of competition with food and feed production, arable land usage, water availability, and other factors. Consequently, lignocellulosic feedstocks such as forest residues, trees from plantations, straws, grasses and other agricultural residues may become viable feedstocks for biofuel production. However, the very heterogeneous nature of lignocellulosic materials that enables them to provide the mechanical support structure of the plants and trees makes them inherently recalcitrant to bioconversion. Also, these materials predominantly contain three separate classes of components as building blocks: cellulose ($C_6$ sugar polymers), hemicellulose (various $C_5$ and $C_6$ sugar polymers), and lignin (aromatic and ether linked hetero polymers).

For example, breaking down these recalcitrant structures to provide fermentable sugars for bioconversion to ethanol typically requires pretreatment steps together with chemical/enzymatic hydrolysis. Furthermore, conventional yeasts are unable to ferment the $C_5$ sugars to ethanol and lignin components are completely unfermentable by such organisms. Often lignin accounts for 25 to 30% of the mass content and 35 to 45% of the chemical energy content of lignocellulosic biomass. For all of these reasons, processes based on a pretreatment/hydrolysis/fermentation path for conversion of lignocellulose biomass to ethanol, for example, are inherently difficult and often uneconomical multi-step and multi conversion processes.

An alternative technology path is to convert lignocellulosic biomass to syngas (also known as synthesis gas, primarily a mix of CO, $H_2$ and $CO_2$ with other components such as $CH_4$, $N_2$, $NH_3$, $H_2S$ and other trace gases) and then ferment this gas with anaerobic microorganisms to produce biofuels such as ethanol, n-butanol or chemicals such as acetic acid, butyric acid and the like. This path can be inherently more efficient than the pretreatment/hydrolysis/fermentation path because the gasification step can convert all of the components to syngas with good efficiency (e.g., greater than 75%), and some strains of anaerobic microorganisms can convert syngas to ethanol, n-butanol or other chemicals with high (e.g., greater than 90% of theoretical) efficiency. Moreover, syngas can be made from many other carbonaceous feedstocks such as natural gas, reformed gas, peat, petroleum coke, coal, solid waste and land fill gas, making this a more universal technology path.

However, this technology path requires that the syngas components CO and $H_2$ be efficiently and economically dissolved in the aqueous medium and transferred to anaerobic microorganisms that convert them to the desired products. And very large quantities of these gases are required. For example, the theoretical equations for CO or $H_2$ to ethanol are:

$$6CO + 3H_2O \rightarrow C_2H_5OH + 4CO_2$$

$$6H_2 + 2CO_2 \rightarrow C_2H_5OH + 3H_2O$$

Thus 6 moles of relatively insoluble gases such as CO or $H_2$ have to transfer to an aqueous medium for each mole of ethanol. Other products such as acetic acid and n-butanol have similar large stoichiometric requirements for the gases.

The anaerobic microorganisms that bring about these bioconversions generate very little metabolic energy from these bioconversions. Consequently they grow very slowly and often continue the conversions during the non-growth phase of their life cycle to gain metabolic energy for their maintenance.

Conversion of syngas to ethanol and other products by free/planktonic cells of anaerobic bacteria have been reported in US 20030211585 A1. Typically in these fermentors the gases are bubbled with agitation into the liquid phase and the bacteria take up the dissolved gases converting them to the product(s).

Many devices and equipment are used for gas transfer to microorganisms in fermentation and waste treatment applications. These numerous bioreactors all suffer from various drawbacks. In most of these conventional bioreactors and systems, agitators with specialized blades or configurations are used. In some others such as gas lift or fluidized beds, liquids or gases are circulated via contacting devices. The agitated vessels require a lot of mechanical power often in the range of 4 to 10 KW per 1000 gallons—uneconomical and unwieldy for large scale fermentations that will be required for such syngas bioconversions. The fluidized or fluid circulating systems cannot provide the required gas dissolution rates. Furthermore, most of these reactors or systems are configured for use with microorganisms in planktonic form i.e. they exist as individual cells in liquid medium.

Furthermore, to get high yields and production rates the cell concentrations in the bioreactor need to be high and this requires some form of cell recycle or retention. Conventionally, this is achieved by filtration of the fermentation broth through microporous or nonporous membranes, returning the cells and purging the excess. These systems are expensive and require extensive maintenance and cleaning of the membranes to maintain the fluxes and other performance parameters.

Cell retention by formation of biofilms is a very good and often inexpensive way to increase the density of microorganisms in bioreactors. This requires a solid matrix with large surface area for the cells to colonize and form a biofilm that contains the metabolizing cells in a matrix of biopolymers that the cells generate. Trickle bed and some fluidized bed bioreactors make use of biofilms to retain microbial cells on solid surfaces while providing dissolved gases in the liquid by flow past the solid matrix. They suffer from either being very large or unable to provide sufficient gas dissolution rates.

Particular forms of membranes have found use in supporting specific types microorganisms for waste water treatment processes. U.S. Pat. No. 4,181,604 discloses the use of hollow fiber membranes for waste treatment where the outer surface of the fibers supports a layer of microorganisms for aerobic digestion of sludge.

In waste treatment applications biofilms with multiple types and classes of microorganisms are formed in natural consortia and such biofilms have been used in membrane bioreactors for waste treatment systems for methane generation, denitrification or treatment of organic wastes. These biofilms are complex structures with multiple classes of organisms with wide variety of metabolisms. For example, for methane formation from organic wastes three distinct classes of organisms—acidogenic bacteria that convert the wastes to mixture of organic acids, syntropic acetogens that convert this mix of acids to acetate and H2/CO2 and methanogenic bacteria that take them to methane and CO2 have to work in close consortia in a biofilm.

None of these fermentations or bioreactor systems shows that by passing syngas over a gas permeable membrane on one side and a single class of anaerobic bacteria on the other side in the liquid phase would lead to the formation of a biofilm of such bacteria that would be stable and would lead to conversion of the syngas to the products. For that to happen, the gases need to permeate with sufficient concentration and rate to support growth and metabolism of the single class of bacteria on the liquid side with simultaneous formation of a biofilm from free/planktonic cells of the single class of bacteria. There is no indication that all of this can occur with a single class of anaerobic bacteria. The body of this patent application and the examples clearly show that this syngas permeation with biofilm formation can be achieved and lead to conversion of syngas components to the desired products.

U.S. Ser. No. 12/036,007 filed Feb. 22, 2008 discloses an asymmetric membrane based bioreactor wherein anaerobic bacteria that have the ability to convert syngas to ethanol or other liquids have formed biopores to the retain biofilms therein on the outer, spongy, surface of the membrane to feed the syngas directly to the bacterial biofilm and not through membrane. U.S. Ser. No. 12/574,499 discloses another membrane based bioreactor wherein anaerobic bacteria that have the ability to convert syngas to ethanol or other liquids have formed on the surface of a membrane to feed the syngas directly to the bacterial biofilm. In either case the lumen of the membrane transports fermentation liquid or broth past the membrane for feeding of nutrients to the biofilm and reflux of liquid products from the biofilm back through the membrane and into the fermentation liquid allow recovery of liquid products.

SUMMARY OF THE INVENTION

It has been found that contacting syngas components such as CO or a mixture of $CO_2$ and $H_2$ with a surface of a membrane and transferring these components in contact with a biofilm consisting of a single genus of anaerobic microorganisms on the opposite side of the membrane will provide a stable system for producing liquid products such as ethanol, butanol and other chemicals. Accordingly this invention is a membrane supported bioreactor system for conversion of syngas components such as CO, $CO_2$ and $H_2$ to liquid fuels and chemicals by a single class of anaerobic microorganisms supported on the surface of the membrane. The gas fed on the membrane's gas contact side transports through the membrane to a biofilm of the anaerobic microorganisms where it is converted to the desired liquid products.

The instant invention uses microporous membranes or non-porous membranes or membranes having similar properties that transfer (dissolve) gases into liquids for delivering the components in the syngas directly to the cells that use the CO and $H_2$ in the gas and transform them into ethanol and other soluble products. The membranes concurrently serve as the support upon which the fermenting cells grow as a biofilm and are thus retained in a concentrated layer. The result is a highly efficient and economical transfer of the feed gas at essentially 100% dissolution and utilization, overcoming limitations for the other fermentation methods and fermenter configurations. The feed gas diffuses through the membrane from the gas side and into the biofilm where it is transformed by the microorganisms to the soluble product of interest. Liquid is passed in the liquid side of the membranes via pumping, stifling or similar means to remove the ethanol and other soluble products formed; the products are recovered via a variety of suitable methods.

A broad embodiment of this invention is a system for converting a feed gas containing at least one of CO or a mixture of $CO_2$ and $H_2$ to a liquid product. The system comprises a bio-support membrane having a gas contacting side in contact with the feed gas for transferring said feed gas across the membrane to a biofilm support side for supporting a microorganism that produces a liquid product. The feed gas supply conduit delivers feed gas to the membrane system through a feed gas chamber having fluid communication with the gas supply conduit and the gas contact side of the membrane for supplying feed gas to said membrane. A liquid retention chamber in fluid communication with the biofilm support side of the membrane maintains a retaining liquid having a redox potential of less than −200 mV in contact with the biofilm. The liquid retention chamber receives liquid products and a liquid recovery conduit in fluid communication with the liquid recovery chamber recovers a liquid product from the membrane system.

An additional embodiment of the instant invention includes the supply of dissolved feed gas in the liquid phase to the side of the biofilm in contact with that phase. This allows dissolved gas substrate to penetrate from both sides of the biofilm and maintains the concentration within the biofilm at higher levels allowing improved reaction rates compared to just supplying the feed gas via the membrane alone. This may be accomplished by pumping a liquid stream where the gases are predissolved into the liquid or by pumping a mixture of liquid containing the syngas present as small bubbles using fine bubble diffusers, jet diffusers or other similar equipment commonly used to transfer gas into liquids. The potential added advantage of using the combined gas and liquid stream is that the additional shear produced by the gas/liquid mixture may be beneficial in controlling the thickness of the biofilm. The advantage of pre-dissolution of the syngas is that very little, if any, of the gas is lost from the system so utilization efficiency is maximized.

Another embodiment of this invention includes the preferential removal of the carbon dioxide ($CO_2$) gas that is formed in the bioconversion process from the syngas using a membrane that selectively permeates $CO_2$ and then returning the syngas enriched in CO and $H_2$ to the bioreactor.

In a further embodiment this invention is a process for converting a feed gas containing at least one of CO or a mixture of $CO_2$ and $H_2$ under anaerobic conditions to a liquid product comprising at least one of ethanol, propanol, n-butanol, acetic acid, propionic acid and butyric acid. The process passes a feed gas comprising a mixture of at least one of CO or a mixture of $CO_2$ and $H_2$ under anaerobic conditions to a gas contacting side of a bio-support membrane for transferring the feed gas across the membrane to a biofilm support side of the bio-support membrane. A fermentation liquid circulates on a biofilm support side of the bio-support membrane, the fermentation liquid having a redox potential of less than −200 mV. A biofilm comprising anaerobic microorganisms of the genus *Clostridium* is maintained on the biofilm support side of the bio-support membrane to convert at least a portion of the feed gas components to a liquid product comprising at least one of ethanol, propanol, n-butanol, acetic acid, propionic acid and butyric acid. The process maintains a pressure differential across the bio-support membrane that avoids the formation of bubbles in the fermentation liquid and prevents wetting of the bio-support membrane on the gas contacting side of the bio-support membrane. The process recovers a liquid product from the fermentation liquid.

DETAILED DESCRIPTION OF THE INVENTION

Bioconversions of CO and $H_2/CO_2$ to acetic acid, ethanol and other products are well known. For example, in a recent book concise description of biochemical pathways and energetics of such bioconversions have been summarized by Das, A. and L. G. Ljungdahl, *Electron Transport System in Acetogens* and by Drake, H. L. and K. Kusel, *Diverse Physiologic Potential of Acetogens*, appearing respectively as Chapters 14 and 13 of Biochemistry and Physiology of Anaerobic Bacteria, L. G. Ljungdahl eds., Springer (2003). Any suitable microorganisms that have the ability to convert the syngas components: CO, $H_2$, $CO_2$ individually or in combination with each other or with other components that are typically present in syngas may be utilized. Suitable microorganisms and/or growth conditions may include those disclosed in U.S. patent application Ser. No. 11/441,392, filed May 25, 2006, entitled "Indirect Or Direct Fermentation of Biomass to Fuel Alcohol," which discloses a biologically pure culture of the microorganism *Clostridium carboxidivorans* having all of the identifying characteristics of ATCC no. BAA-624; and U.S. patent application Ser. No. 11/514,385 filed Aug. 31, 2006 entitled "Isolation and Characterization of Novel Clostridial Species," which discloses a biologically pure culture of the microorganism *Clostridium ragsdalei* having all of the identifying characteristics of ATCC No. BAA-622; both of which are incorporated herein by reference in their entirety. *Clostridium carboxidivorans* may be used, for example, to ferment syngas to ethanol and/or n-butanol. *Clostridium ragsdalei* may be used, for example, to ferment syngas to ethanol.

Suitable microorganisms and growth conditions include the anaerobic bacteria *Butyribacterium methylotrophicum*, having the identifying characteristics of ATCC 33266 which can be adapted to CO and used and this will enable the production of n-butanol as well as butyric acid as taught in the references: "Evidence for Production of n-Butanol from Carbon Monoxide by *Butyribacterium methylotrophicum*," Journal of Fermentation and Bioengineering, vol. 72, 1991, p. 58-60; "Production of butanol and ethanol from synthesis gas via fermentation," FUEL, vol. 70, May 1991, p. 615-619. Other suitable microorganisms include *Clostridium Ljungdahli*, with strains having the identifying characteristics of ATCC 49587 (U.S. Pat. No. 5,173,429) and ATCC 55988 and 55989 (U.S. Pat. No. 6,136,577) which enable the production of ethanol as well as acetic acid; *Clostridium autoethanogenum* sp. nov., an anaerobic bacterium that produces ethanol from syngas Jamal Abrini, Henry Naveau, Edmond-Jacques Nyns, Arch Microbiol., 1994, 345-351; Archives of Microbiology 1994, 161: 345-351; and *Clostridium Coskatii* as disclosed in copending application U.S. Ser. No. 12/727,320 filed Mar. 19, 2010. All of these references are incorporated herein in their entirety.

Suitable conditions will also require relatively pure mono-cultures or co-cultures of the anaerobic microorganisms that make up the biofilm. Therefore the microorganism will typically consist essentially of a single anaerobic strain of microorganism. The relatively pure mono-cultures or co-cultures provide a desired selectivity to specifically desired product components and are necessary to minimize the presence of other microorganisms that can contaminate the liquid products. In most cases the microorganism will consist essentially of a mono-culture of the anaerobic microorganism. The preferred microorganisms maintained on the bio-support membrane comprise mono-cultures or co-cultures of at least one of *Clostridium Ragsdalei, Clostridium autoethanogenum, Clostridium Coskatii, Butyribacterium methylotrophicum,* and *Clostridium Ljungdahlii*. Microorganisms consisting essentially of anaerobic microorganisms from the genus *Clostridium* are particularly preferred.

The microorganisms found suitable thus far for this invention require anaerobic growth conditions. Therefore the system will employ suitable control and sealing methods to limit the introduction of oxygen into the system. Since the organisms reside principally in contact with the liquid volume of the retention chamber the system maintains a suitable redox potential in the liquid and this chamber may be monitored to make insure anaerobic conditions. Anaerobic conditions in the retained liquid volume are usually defined as having a redox potential of less than −200 mV and preferably a redox potential in the range of from −300 to −500 mV. To further minimize exposure of the microorganisms to oxygen, the feed gas will preferably have an oxygen concentration of less than 1000 ppm, more preferably less than 100 ppm, and even more preferably less than 10 ppm.

The instant invention uses microporous membranes or non-porous membranes or membranes having similar properties in being able to transfer (dissolve) gases into liquids for delivering the components in the syngas directly to the cells that use the CO and $H_2$ in the gas and transform them into ethanol and other soluble products. The membranes concurrently serve as the support upon which the fermenting cells grow as a biofilm and are thus retained in a concentrated layer.

The result is a highly efficient and economical transfer of the syngas at essentially 100% dissolution and utilization, overcoming limitations for the other fermentation methods and fermenter configurations. The syngas diffuses through the membrane from the gas side and into the biofilm where it is transformed by the microbes to the soluble product of interest. Liquid is passed in the liquid side of the membranes via pumping, stifling or similar means to remove the ethanol and other soluble products formed; the products are recovered via a variety of suitable methods.

Microporous membranes made from polymers or ceramics have been recently developed and commercialized for wastewater treatment and purification applications. Some variations of these have also been developed for aeration or oxygenation of liquids. Typically these membranes are made from hydrophobic polymers such as polyethylene or polypropylene which are processed to create a fine porous structure in the polymer film. Many commercial organizations supply such membranes primarily in two important geometries—hollow fiber and flat sheets. These can then be made into modules by appropriate potting and fitting and these modules have very high surface area of pores in small volumes.

Suitable hydrophobic microporous hollow fiber membranes have been used for degassing applications to remove oxygen, carbon dioxide, and other gases from water and other liquids. An example of commercial membrane modules for such applications is the Liqui-Cel® membrane contactor from Membrana (Charlotte, N.C.), containing the polypropylene (PP) X40 or X50 hollow fibers. CELGARD® microporous PP hollow fiber membrane, containing the X30 fibers, is also available from Membrana for oxygenation applications. Liqui-Cel® membrane modules suitable for large scale industrial applications have large membrane surface areas (e.g., 220 $m^2$ active membrane surface area for Liqui-Cel® Industrial 14×28). Some characteristics of these fibers are given in the Table 1 below.

TABLE 1

|  | X30 | X40 | X50 |
|---|---|---|---|
| Porosity (nominal) | 40% | 25% | 40% |
| Pore Size | 0.03 μm | 0.04 μm | 0.04 μm |
| Internal Diameter | 240 μm | 200 μm | 220 μm |
| Outer Diameter | 300 μm | 300 μm | 300 μm |
| Wall Thickness | 30 μm | 50 μm | 40 μm |

A microporous PP hollow fiber membrane product (CellGas® module) is available from Spectrum Laboratories (Rancho Dominguez, Calif.) for gentle oxygenation of bioreactors without excessive shear to the microbial or cell cultures. This PP hollow fiber is hydrophobic, with a nominal pore size of 0.05 μm and a fiber inner diameter of 0.2 mm.

For the use of hydrophobic microporous membranes for afore-mentioned applications, it is necessary to properly manage the pressure difference across the membrane to avoid formation of bubbles in the liquid. If the pressure difference is greater than a critical pressure, the value of which depends on properties of the liquid and the membrane, liquid can enter the pore ("wetting") and the gas transfer rate is significantly impeded.

To prevent wetting of pores during operations, some composite membranes have been developed by the membrane suppliers. The SuperPhobic® membrane contactor from Membrana keeps the gas phase and liquid phase independent by placing a physical barrier in the form of a gas-permeable non-porous membrane layer on the membrane surface that contacts the process liquid. The SuperPhobic® 4×28 module contains 21.7 $m^2$ of membrane surface area. Another composite hollow fiber membrane with an ultra-thin nonporous membrane sandwiched between two porous membranes is available from Mitsubishi Rayon (Model MHF3504) in the form of composite hollow fibers having at 34 $m^2$ membrane area per module.

Non-porous (dense) polymeric membranes have been used commercially for various gas separation applications. These membranes separate gases by the selective permeation across the membrane wall. The solubility in the membrane material and the rate of diffusion through the molecular free volume in the membrane wall determine its permeation rate for each gas. Gases that exhibit high solubility in the membranes and gasses that are small in molecular size permeate faster than larger, less soluble gases. Therefore, the desired gas separation is achieved by using membranes with suitable selectivity in conjunction with appropriate operating conditions. For example, Hydrogen Membranes from Medal (Newport, Del.) are used in recovery or purification of hydrogen with preferential permeation of hydrogen and $CO_2$. Medal also provides membranes for $CO_2$ removal with preferential permeation of $CO_2$.

Microporous membranes have been used widely in membrane bioreactors for wastewater treatment. Installations are mostly in the submerged membrane configuration using hollow fiber or flat sheet membranes for wastewater treatment. The structure and module configuration of these membranes may prove particularly useful for the systems of this invention. The membranes are typically made of poly(vinylidene fluoride) (PVDF), polysulfone (PS), polyethersulfone (PES), polyethylene (PE), polypropylene (PP), poly(vinyl chloride) (PVC), or other polymeric materials. The pore size of the hydrophilic membrane is usually less than 0.5 μm, preferably less than 0.4 μm, more preferably less than 0.25 μm and most preferably in the ultrafiltration range of nominal MWCO of 10 to 500 kDa and more preferably in the range of 50 to 300 kDa. A typical pore size range is from 0.01 to 0.5 μm. The typical hollow fiber outer diameter is 0.4 to 2.8 mm and inner diameter 0.3 to 1.2 mm. For this invention, a pore size of 0.2 micron or less is desirable. In these submerged membrane configurations, wastewater containing contaminants are fed into a tank and treated water is filtered through the membrane with a suction pressure applied to the filtrate side (the lumen side of the hollow fiber or the center of the flat plate) of the membrane. Typically the tank retains multiple membrane modules submerged without an individual housing. There are a number of commercial suppliers of membranes for submerged membrane bioreactors in wastewater treatment, each with some distinct features in membrane geometry and module design as described below. These membrane geometries and module designs can be suitable for the instant invention and are incorporated herein.

A hollow fiber membrane SteraporeSUN™, available from Mistubishi Rayon (Tokyo, Japan), is made of PE with modified hydrophilic membrane surface. The hollow fiber has a nominal pore size of 0.4 μm and a fiber outer diameter of 0.54 mm. A SteraporeSUN™ membrane unit Model SUN21034LAN has a total membrane surface area of 210 $m^2$, containing 70 membrane elements Model SUR334LA, each with 3 $m^2$ membrane area.

The Microza® membranes from Asahi Kasei Chemicals (Tokyo, Japan) are hydrophilic hollow fiber membranes available in the ultrafiltration (MWCO 3,000 to 80,000) and microfiltration (0.1 to 0.25 μm) ranges. The Microza® ultrafiltration membranes have a "double skin" construction with a selective skin layer on both the inner and outer surface of the hollow fibers. Thus, the Microza® membranes, both the ultrafiltration and microfiltration types, can be used for both outside-in and inside-out filtration modes.

Another commercial hydrophilic hollow fiber membrane is the PVDF microfiltration membrane used for water filtration in the MEMCOR® CS submerged membrane systems from Siemens Water Technologies (Shrewsbury, Mass.). Another commercial hydrophilic hollow fiber membranes is the Zenon ZeeWeed® 500 membranes from GE Water & Process Technologies (Oakville, Ontario, Canada), which is a reinforced, composite membrane, comprising a porous woven inner support and a selective ultrafiltration layer made of PVDF coated on the outer surface of the support. Both the MEMCOR® CS membranes and the Zenon ZeeWeed® membranes are typically used in the outside-in filtration mode, rejecting microorganisms and other contaminants at the outer surface of the hollow fibers.

Another hollow fiber membrane SteraporeSADF™ is available from Mitsubishi Rayon. This membrane is made of PVDF with a nominal pore size of 0.4 μm and a fiber outer diameter of 2.8 mm. Each SteraporeSADF™ membrane element Model SADF2590 contains 25 $m^2$ membrane surface area, and each StreraporeSADF™ membrane unit Model SA50090APE06 containing 20 SADF2590 membrane elements has a total membrane surface area of 500 $m^2$.

Kubota Corporation (Tokyo, Japan) markets submerged membrane systems for membrane bioreactors. These membranes are of the flat-plate configuration and made of PVC with a pore size of 0.4 μm. Each membrane cartridge has 0.8 $m^2$ membrane surface area, and a Model EK-400 membrane unit, containing 400 membrane cartridges, has a total membrane area of 320 $m^2$.

Membranes of the various geometries and compositions described above may be used in arrangements of unitary arrays or assemblies of varied composition in the process and system of this invention. Thus bio-support membrane used in the instant invention can be microporous, non-porous, or composite membranes or any combination thereof. Any suitable potting technique can be used to collect and provide the necessary assembly of individual membrane elements. If microporous, hydrophobic membranes are preferred due to faster diffusion of gases in the gas-filled pores than liquid-filled pores.

The feed gas flows through the gas chamber of the membrane unit continuously or intermittently. The feed gas pressure is in the range of 1 to 1000 psia, preferably 5 to 400 psia, and most preferably 10 to 200 psia. Operating at higher gas pressures has the advantage of increasing the solubilities of gases in the liquid and potentially increasing the rates of gas transfer and bioconversion. The differential pressure between the liquid and gas phases is managed in a manner that the membrane integrity is not compromised (e.g., the burst strength of the membrane is not exceeded) and the desired gas-liquid interface phase is maintained.

In such membranes the gas and liquid can be brought into direct and intimate contact without creating any bubbles by operating at a differential pressure that is below the bubble point of the membrane liquid interface and maintains the gas-liquid interface. Furthermore, the properties of this interface can be controlled by the porosity and hydrophobicity/hydrophlicity properties of the membrane pores.

Figure 1:
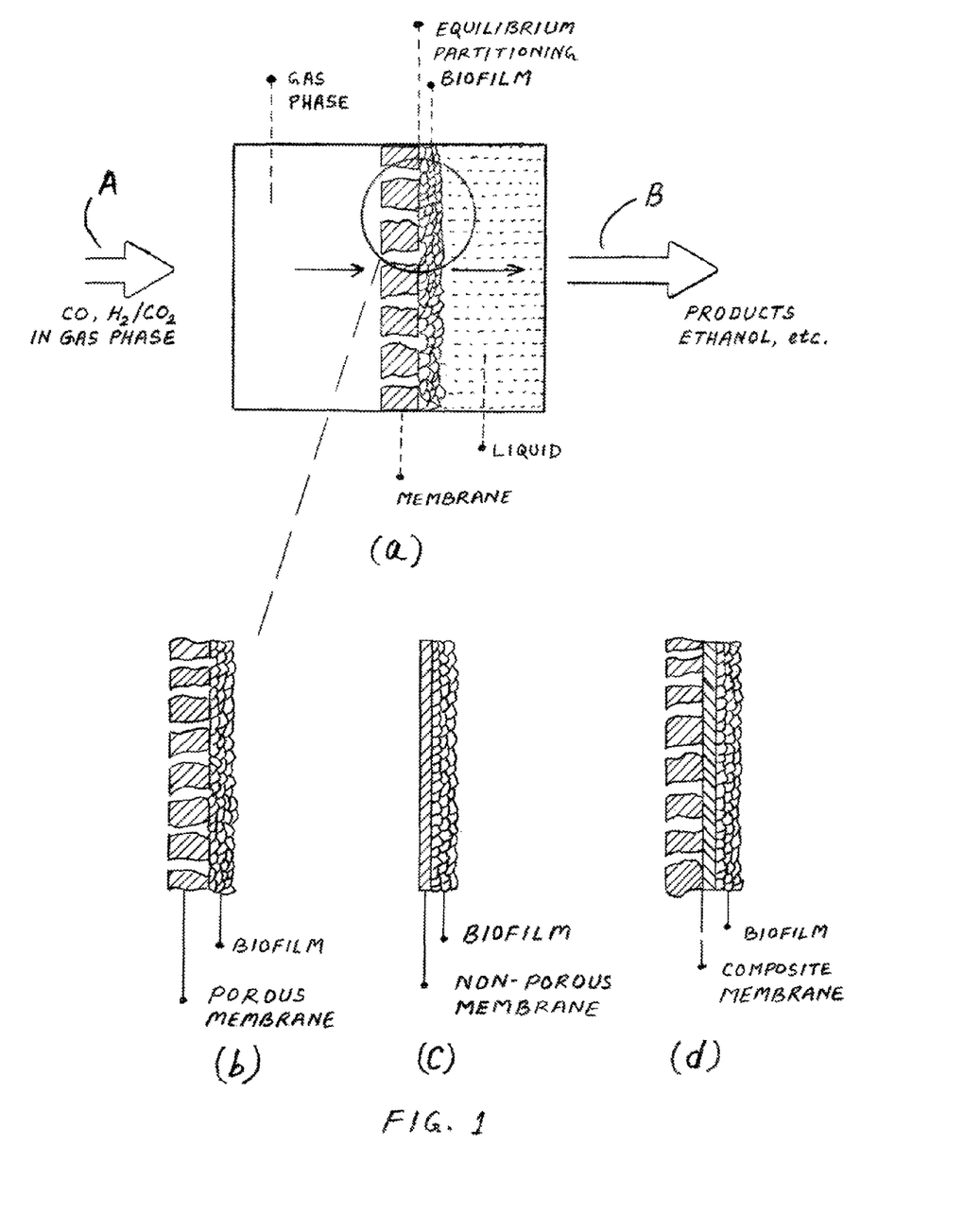
FIG. 1 is a schematic drawing showing gas diffusing through a porous membrane into a liquid and details of a porous membrane, non-porous membrane and composite membrane.

In this invention, a bio-support membrane suitable for permeation of at least one of CO or a mixture of $H_2$ and $CO_2$ provides the separation between a feed gas and a liquid phase. FIG. 1 shows more detail of the membrane configuration and interface in the operation of a representative bio-reactor system. FIG. 1(a) depicts syngas stream A flowing to the gas feed side of the membrane in gas phase maintained in a chamber on the gas contact side of the membrane. The syngas components freely diffuse through the membrane pores to the liquid interface but without formation of bubbles. The anaerobic acetogenic bacteria, *Clostridium ragsdaeli*, having all of the identifying characteristics of ATCC No. BAA-622, is maintained in a fermentation media. The fermentation media is circulated through a chamber on the opposite side of the membrane that maintains a liquid volume in contact with the liquid side of the membrane. Suitable microbial cells are present as bio-film on the liquid-contacting side of the membrane surface, converting at least one of CO or $H_2/CO_2$ in the feed gas to desirable products. Since the membrane pores are much smaller than the width of the microorganisms they preferentially stay on the membrane surface to convert CO and $H_2/CO_2$ to gain metabolic energy, grow and form a bio-film on the membrane surface. A stream B withdraws the liquid phase components from a liquid volume retained about the outer surface of the biofilm.

FIGS. 1(b)-(c) show various forms of the membrane with a biofilm present on the liquid contacting side of the membrane. The membrane portions of FIGS. 1(a) and 1(b) both schematically show a cross-section of porous membrane to the left with a biofilm layer developed on the opposite side of the membrane. The interface between the biofilm and the membrane functions as equilibrium partitioning to keep the liquid and gas phases separated from each other. FIG. 1(c) depicts a similar arrangement however this time with a nonporous membrane to the left and a biofilm adhering to the surface on the right-hand side of the membrane. FIG. 1(d) illustrates a composite structure for the membrane that positions a porous membrane surface in contact with the gas phase components. The opposite face (right side) of the porous membrane retains a nonporous membrane layer and a biofilm layer adheres to the surface on the right side of the non-porous membrane layer.

Figure 2:
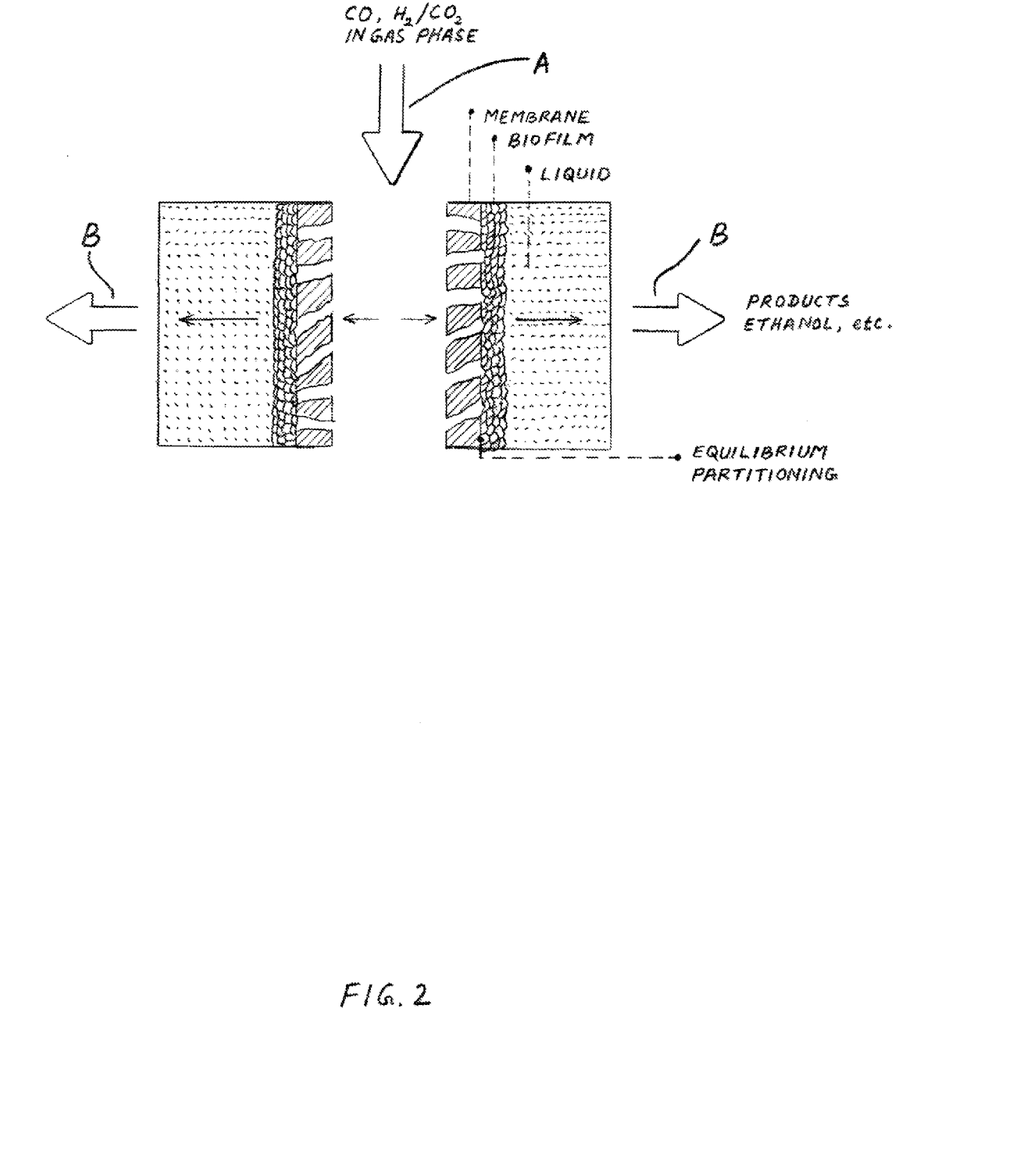
FIG. 2 is a schematic drawing showing a central passage delivering gas to two parallel membrane walls with a liquid phase to the outside of each wall.

FIG. 2 depicts a generalized view of a typical flow arrangement for efficient use of space in a membrane system. Syngas components enter the system as gas stream A and flow into a central space between two membrane walls. Gas phase contact surfaces of the opposing membrane walls form a distribution chamber for receiving gas from stream A. Gas permeates simultaneous through, in this case, the porous membrane for consumption by the microbes in the biofilm layers that adhere to the outer walls of the two opposing membranes. In this manner each gas channel serves multiple membrane surfaces and the stream B of liquid products is delivered from multiple membrane walls. The arrangement of FIG. 2 can use a flat sheet configuration and be particularly useful for good flow control and distribution on the liquid side that may be necessary for biofilm thickness control.

Figure 3:
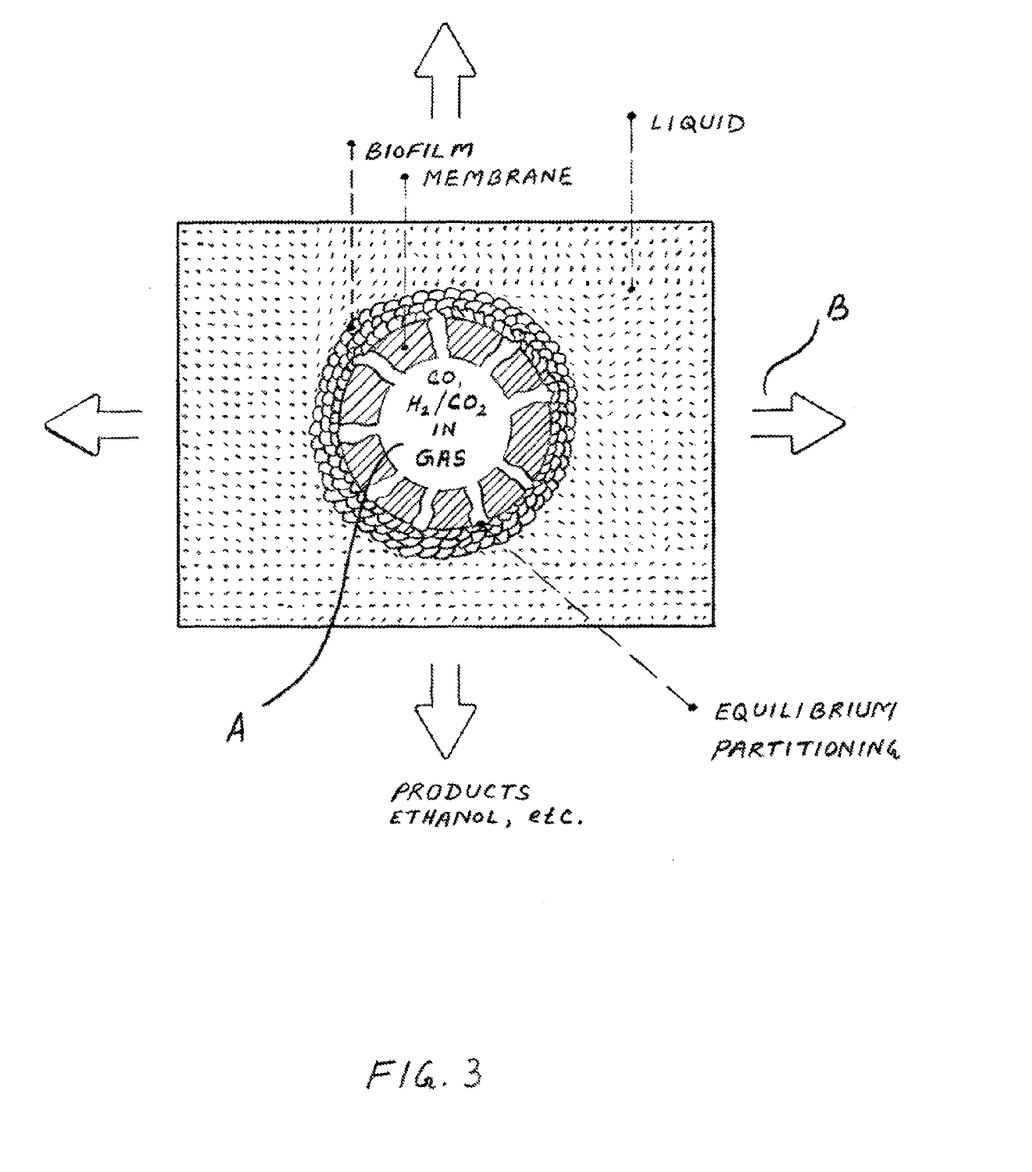
FIG. 3 is a schematic drawing showing the interior passage of FIG. 2 enclosed by the interior surface of the membrane in tubular form with liquid retained to around the membrane circumference.

FIG. 3 shows the special case of FIG. 2 wherein the opposite wall of the central distribution chamber wrap around in continuous form to provide a tubular membrane. In this case gas stream A enters the lumen of the membrane and streams B of liquid products flow away from the outer walls in all directions. Hollow fibers are particularly useful for such bioreactor configuration.

Figure 4:
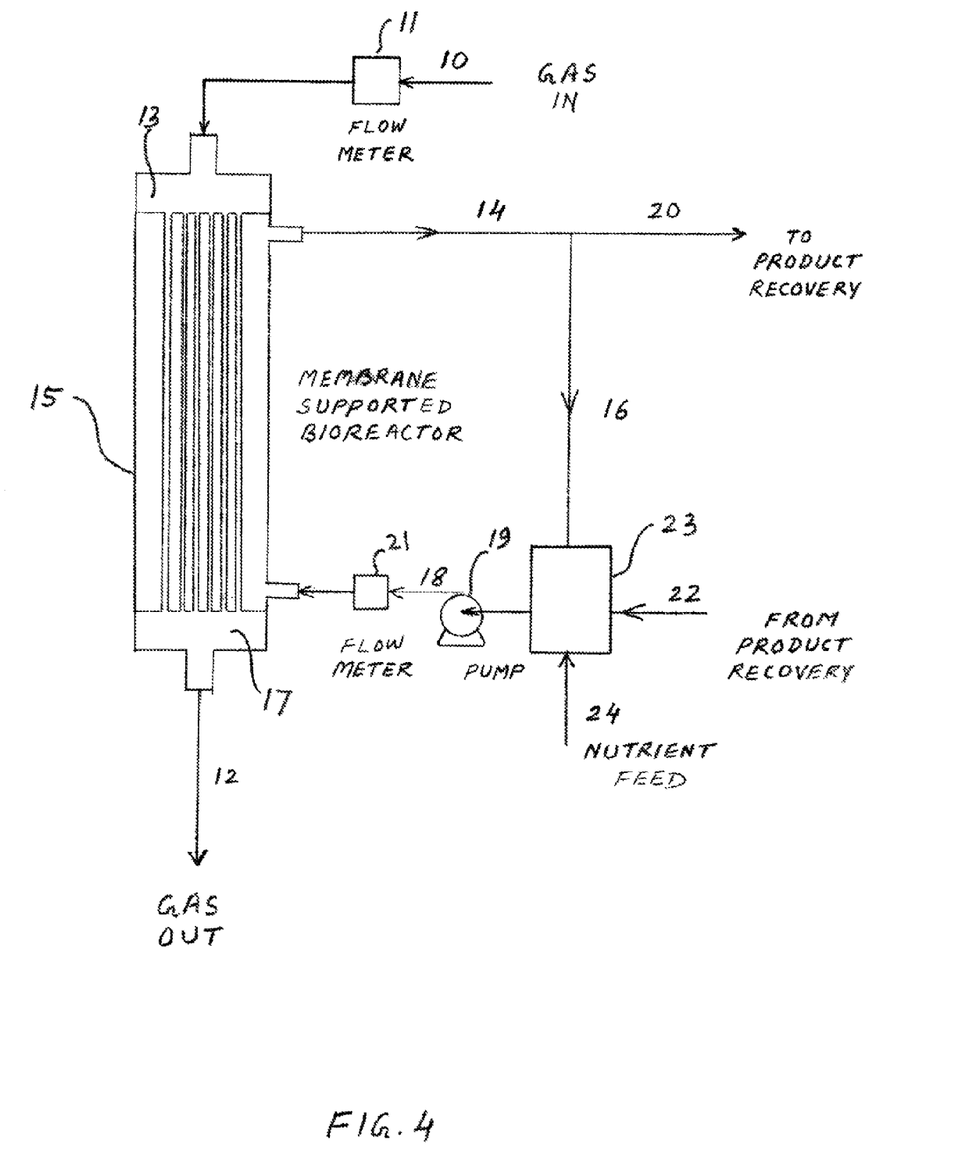
FIG. 4 is a schematic drawing showing a bioreactor system with gas and liquid circulation.

FIG. 4 illustrates a specific configuration of one embodiment of this invention. A gas supply conduit delivers a feed gas Stream 10 containing CO, $H_2$, and $CO_2$ at a rate recorded by a flow meter 11. A feed gas distribution chamber 13 receives the feed gas stream and distributes the feed to the lumens of tubular membranes in a membrane unit 15 that provides a membrane supported bioreactor. A collection chamber 17 collects a portion of the feed gas that exits the lumens and an exhaust gas stream 12 from chamber 17 exits the membrane unit.

A tank surrounds the outside of the tubular membrane elements in the membrane supported bioreactor and retains a liquid for growth and maintenance of a biofilm layer on the outer surface of the membrane. The tank provides the means of temperature and pH controls for the liquid, which contains nutrients needed to sustain the activity of the microbial cells. The liquid in the tank is stirred to provide adequate mixing and sparged with a suitable gas, if necessary, to maintain a suitable gaseous environment. A re-circulating liquid loop, consisting of Streams 14, 16, and 18 re-circulates liquid through the tank. Liquid flows from the tank through lines 14 and 16 while line 20 withdraws liquid and takes it to product recovery to recover liquid products. Line 18 returns the remaining liquid from line 16 to the tank via pump 19 at rate recorded by flow meter 21.

The product recovery step removes the desirable product from Stream 20, while leaving substantial amounts of water and residual nutrients in the treated stream, part of which is returned to the bioreactor system via line 22. A nutrient feed is added via line 24, as needed, to compensate for the amount of water removed and to replenish nutrients. Chamber 23 provides any mixing of the various streams before return to the tank via line 18.

The flow rates of Streams 18 and 14, recirculated through the membrane unit, are selected so that there is no significant liquid boundary layer that impedes mass transfer near the liquid-facing side of the membrane and there is no excessive shear that may severely limit the attachment of cells and formation of the biofilm on the membrane surface. The superficial linear velocity of the liquid tangential to the membrane should be in the range of 0.01 to 20 cm/s, preferably 0.05 to 5 cm/s, and most preferably 0.2 to 1.0 cm/s. In addition to the liquid linear velocity, the biofilm thickness can be controlled by other means to create shear on the liquid-biofilm interface, including scouring of the external membrane surface with gas bubbles and free movement of the hollow fibers. Also, operating conditions that affect the metabolic activity of the microbial cells and the mass transfer rates of gases and nutrients can be manipulated to control the biofilm thickness. The biofilm thickness in the instant invention is in the range of 5-500 µm, preferably 5-200 µm.

Depending on the nature of the desired product, there are a number of technologies that can be used for product recovery. For example, distillation, dephlegmation, pervaporation and liquid-liquid extraction can be used for the recovery of ethanol and n-butanol, whereas electrodialysis and ion-exchange can be used for the recovery of acetate, butyrate, and other ionic products.

In all the depicted arrangements the CO an $H_2$ from the syngas are utilized and a gradient for their transport from the gas feed side is created due to biochemical reaction at the membrane liquid interface. This reaction creates liquid fuel or chemicals such as ethanol and acetic acid which diffuse into the liquid and are removed via circulation of the liquid past the biofilm. Thus the very large surface areas of the membrane pores are usable for gas transfer to the biofilm and the product is recovered from the liquid side. Furthermore, the reaction rate, gas concentration gradient and the thickness of the biofilm can be maintained in equilibrium because the microorganisms in the biofilm will maintain itself only up to the layer where the gas is available.

The membranes can be configured into typical modules as shown as an example in FIG. 4 for hollow fibers. The gas flows in the fine fibers that are bundled and potted inside a cylindrical shell or vessel through which the liquid is distributed and circulated. Very high surface areas in the range of 1000 m2 to 5000 m2 per m3 can be achieved in such modules.

The bioreactor modules can be operated multi-stage operation of fermentation using the modules in counter-current, co-current or a combination thereof mode between the gas and the liquid. In the example as shown in FIG. 4 a counter current operation is depicted.

During the bioconversion excess $CO_2$ is generated and this gas can diffuse back and dilute out the concentrations of CO and $H_2$ in the feed gas and thus reduce their mass transfer rates. Other types of membranes that preferentially permeate $CO_2$ over CO and $H_2$ can be used in the multi stage configuration as shown as an example in FIG. 5 where, using a membrane that selectively permeates $CO_2$ and then returning the syngas enriched in CO and $H_2$ to the bioreactor can be achieved.

Figure 5:
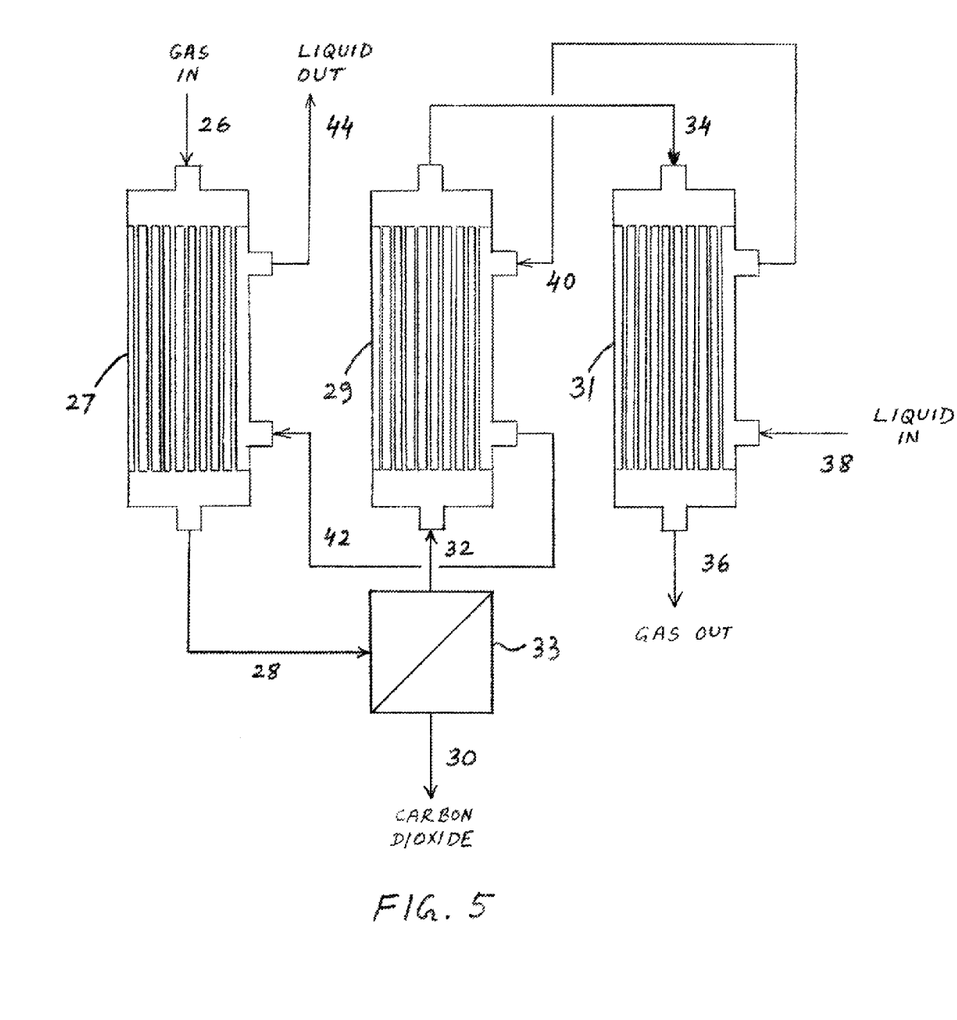
FIG. 5 is a schematic drawing showing a bioreactor system with multiple bioreactors arranged in series having intermediate carbon dioxide removal.

FIG. 5 depicts a system where the entering feed gas flows into bioreactor 27 via line 26 and serially through bioreactors 29 and 31 via lines 28, 32 and 34. At the same time liquid that contacts the biofilm layers enters the system via line 38 and flows countercurrently, with respect to the gas flow, through bioreactors 31, 29 and 27 via lines 40 and 42. Liquid products are recovered from the liquid flowing out of line 40 and gas stream is withdrawn from the system via line 36. Separation unit 33 provides the stream of line 28 with intermediate removal of $CO_2$ from the system via any suitable device or process such as a membrane or extraction step. Interconnecting lines 40 and 42 also provide the function of establishing continuous communication through all of the lumens of the different bioreactors so that any combined collection and distribution chambers provide a continuous flow path.

Other microorganisms can also be used in the examples and configurations described above, including those specifically identified in the foregoing description.

Example

A Liqui-Cel® membrane contactor MiniModule® 1×5.5 from Membrana (Charlotte, N.C.) is used as a membrane supported bioreactor for the conversion of carbon monoxide and hydrogen into ethanol. This membrane module contains X50 microporous hydrophobic polypropylene hollow fibers with 40% porosity and 0.04 µm pore size. The fiber outer diameter is 300 µm and internal diameter 220 µm. The active membrane surface area of the module is 0.18 $m^2$. A gas containing 40% CO, 30% $H_2$, and 30% $CO_2$ is fed to the lumen of the fibers at 60 std ml/min and 2 psig inlet pressure and the residual gas exits the module at 1 psig outlet pressure. The membrane module is connected to a 3-liter BioFlo® 110 Fermentor from New Brunswick Scientific (Edison, N.J.). The fermentation medium having the composition given in Table 2 is pumped from the fermentor, flows through the shell side of the membrane module, and returns to the fermentor. The flow rate of this recirculating medium is 180 ml/min, and the pressure at the outlet of the membrane module is maintained at 5 psig by adjusting a back-pressure valve. The fermentor contains 2 liters of the fermentation medium, which is agitated at 100 rpm and maintained at 37° c. The fermentor is maintained under anaerobic conditions.

The fresh fermentation medium contains the components listed in Tables 2 & 3(a)-(d). Initially, the bioreactor system is operated in the batch mode and inoculated with 200 ml of an active culture of *Clostridium ragsdalei* ATCC No. BAA-622. The fermentation pH is controlled at pH 5.9 in the first 24 hours by addition of 1 N $NaHCO_3$ to favor cell growth and then allowed to drop without control until it reaches pH 4.5 to favor ethanol production. The system remains in the batch mode for 10 days to establish the attachment of the microbial cells on the membrane surface. Then, the system is switched to continuous operation, with continuous withdrawal of the fermentation broth for product recovery and replenish of fresh medium. With the continuous operation, suspended cells in the fermentation broth are gradually removed from the bioreactor system and decrease in concentration, while the biofilm attached on the membrane surface continues to grow until the biofilm reaches a thickness equilibrated with the operating conditions. The ethanol concentration at the end of the 10-day batch operation is 5 g/L. At the beginning of the continuous operation, a low broth withdrawal rate is selected so that the ethanol concentration in the broth does not decrease but increases with time. The broth withdrawal rate is then gradually increased. After 20 days of continuous operation, the ethanol concentration increases to 10 g/L with the broth withdrawal rate at 20 ml/hr.

TABLE 2

Fermentation Medium Compositions

| Components | Amount per liter |
|---|---|
| Mineral solution, See Table 2(a) | 25 ml |
| Trace metal solution, See Table 2(b) | 10 ml |
| Vitamins solution, See Table 2(c) | 10 ml |
| Yeast Extract | 0.5 g |
| Adjust pH with NaOH | 6.1 |
| Reducing agent, See Table 2(d) | 2.5 ml |

TABLE 3(a)

Mineral Solution

| Components | Concentration (g/L) |
|---|---|
| NaCl | 80 |
| $NH_4Cl$ | 100 |
| KCl | 10 |
| $KH_2PO_4$ | 10 |
| $MgSO_4 \cdot 7H_2O$ | 20 |
| $CaCl_2 \cdot 2H_2O$ | 4 |

TABLE 3(b)

Trace Metals Solution

| Components | Concentration (g/L) |
|---|---|
| Nitrilotriacetic acid | 2.0 |
| Adjust the pH to 6.0 with KOH | |
| $MnSO_4 \cdot H_2O$ | 1.0 |
| $Fe(NH_4)_2(SO_4)_2 \cdot 6H_2O$ | 0.8 |
| $CoCl_2 \cdot 6H_2O$ | 0.2 |
| $ZnSO_4 \cdot 7H_2O$ | 1.0 |
| $NiCl_2 \cdot 6H_2O$ | 0.2 |
| $Na_2MoO_4 \cdot 2H_2O$ | 0.02 |
| $Na_2SeO_4$ | 0.1 |
| $Na_2WO_4$ | 0.2 |

TABLE 3(c)

Vitamin Solution

| Components | Concentration (mg/L) |
|---|---|
| Pyridoxine·HCl | 10 |
| Thiamine·HCl | 5 |
| Riboflavin | 5 |
| Calcium Pantothenate | 5 |
| Thioctic acid | 5 |
| p-Aminobenzoic acid | 5 |
| Nicotinic acid | 5 |
| Vitamin B12 | 5 |
| Mercaptoethanesulfonic acid | 5 |
| Biotin | 2 |
| Folic acid | 2 |

TABLE 3(d)

Reducing Agent

| Components | Concentration (g/L) |
|---|---|
| Cysteine (free base) | 40 |
| $Na_2S \cdot 9H_2O$ | 40 |

The example shows that passing a syngas over a gas permeable membrane on one side and a single class of anaerobic bacteria on the other side in the liquid phase will enable the stable formation of a biofilm of such bacteria that produces liquid products from components of syngas. Thus syngas permeation with biofilm formation can be achieved through a membrane and will provide conversion of syngas components to desired liquid products.

The invention claimed is:

1. A process for converting a feed gas containing at least one of CO or a mixture of $CO_2$ and $H_2$ under anaerobic conditions to a liquid product comprising at least one of ethanol, propanol, n-butanol, acetic acid, propionic acid and butyric acid:
    a) passing a feed gas comprising a mixture of at least one of CO or a mixture of $CO_2$ and $H_2$ under anaerobic conditions to a gas contacting side of a bio-support membrane for transferring the feed gas across the membrane to a biofilm support side of the bio support membrane;
    b) circulating a fermentation liquid on the biofilm support side of the bio-support membrane, the fermentation liquid having a redox potential of less than −200 mV;
    c) maintaining a biofilm consisting essentially of anaerobic microorganisms on the biofilm support side of the bio-support membrane to convert at least a portion of the feed gas components to a liquid product comprising at least one of ethanol, propanol, n-butanol, acetic acid, propionic acid and butyric acid;
    d) maintaining a pressure differential across the bio-support membrane that avoids the formation of bubbles in the fermentation liquid and prevents wetting of the bio-support membrane on the gas contacting side of the bio-support membrane; and,
    e) recovering a liquid product from the fermentation liquid.

2. The process of claim 1 wherein the bio-support membranes comprises a micro porous membrane and/or a non-porous membrane.

3. The process of claim 1 wherein the microorganisms produce a liquid product comprising ethanol.

4. The process of claim 1 wherein the feed gas is synthesis gas having an oxygen concentration of less than 1000 ppm, the fermentation liquid has a redox potential in the range of −300 mV to −500 mV and the biofilm support side of the membrane supports the microorganisms that produces ethanol.

5. The process of claim 1 wherein the fermentation liquid contains one or more dissolved gases for contact with the biofilm and the dissolved gases include at least one of CO and $CO_2$ and $H_2$.

6. The process of claim 1 wherein the fermentation liquid is agitated against the biofilm support side of the biosupport membrane to provide shear forces to control the thickness of the biofilm.

7. The process of claim 1 wherein the feed gas passes serially through multiple bio-support membranes, the process includes at least one feed gas chamber for each bio-support membrane and $CO_2$ is removed from the feed gas as it passes between bio-support membranes.

8. The process of claim 1 wherein the bio-support membrane is hydrophobic.

9. The process of claim 1 wherein the bio-support membrane comprises a plurality of hollow fiber membranes and a feed gas chamber that includes a collective lumen volume of the fibers distributes the feed gas to lumens of the membranes in the bio-support membrane.

10. The process of claim 7 wherein a liquid chamber retains the fermentation liquid on the gas contacting side of the bio-support membrane and the liquid chamber includes hollow fibers membranes for removing dissolved $CO_2$ from the liquid phase.

11. The process of claim 1 wherein the microorganisms maintained on the bio-support membrane consist essentially of a mono-culture or a co-culture of at least one of *Clostridium Ragsdalei, Clostridium autoethanogenum, Clostridium Coskatii, Butyribacterium methylotrophicum*, and *Clostridium Ljungdahlii*.

12. The process of claim 1 wherein the microorganisms maintained on the bio-support side of the membrane consist essentially of anaerobic microorganisms from the genus *Clostridium*.

13. The process of claim 1 wherein the microorganisms consist essentially of a mono-culture of anaerobic microorganisms from the genus *Clostridium*.

14. The process of claim 1 wherein a continuous flow of feed gas having an oxygen concentration of less than 100 ppm passes across the gas contact side of the bio-support membrane.

15. A process for converting a feed gas containing at least one of CO or a mixture of $CO_2$ and $H_2$ to a liquid product comprising:
   a) delivering feed gas to a gas distribution chamber;
   b) distributing the feed gas from the distribution chamber to lumens of a plurality of hollow fiber membranes;
   c) surrounding the plurality of hollow fiber membranes with a fermentation liquid having a redox potential of less than −200 mV;
   d) maintaining a biofilm consisting essentially of anaerobic microorganisms from the genus *Clostridium* on the outer surface of the plurality of hollow fiber membranes for producing liquid products from a synthesis gas;
   e) diffusing feed gas from the lumens across the membrane and into the biofilm to convert at least a portion of the synthesis gas to liquid products comprising at least one of ethanol, propanol, n-butanol, acetic acid, propionic acid and butyric acid;
   f) maintaining a pressure differential across a bio-support membrane that prevents the formation of bubbles of feed gas components from the lumens in the fermentation liquid and prevents wetting of the outer surface of the membrane; and,
   g) passing a portion of a fermentation broth to a separation zone and recovering liquid products from the separation zone.

16. The process of claim 15 wherein the hollow fiber membranes comprise a micro porous membrane and/or a non-porous membrane.

17. The process of claim 15 wherein the feed gas comprises synthesis gas and the microorganisms produce a liquid product comprising at least one of ethanol, n-butanol, acetic acid, and butyric acid.

18. The process of claim 15 wherein the feed gas has an oxygen concentration of less than 100 ppm, the fermentation liquid has a redox potential in the range of from −300 mV to −500 mV, the microorganisms produces ethanol and the separation zone recovers an ethanol containing liquid.

19. The process of claim 15 wherein the fermentation liquid contains one or more dissolved gases comprising one or more components of the synthesis gas that enter the fermentation liquid in solution.

20. The process of claim 15 wherein feed gas passes serially through a plurality of gas distribution chambers that each distribute feed gas to the plurality of hollow fiber membranes, the process includes a collection chamber for each distribution chamber that serially receives feed gas discharged from the lumens of the plurality of hollow fiber membranes, and $CO_2$ is removed from the feed gas as it passes from at least one collection chamber to at least one distribution chamber.

21. The process of claim 15 wherein the microorganisms maintained on the bio-support membrane consist essentially of a mono-culture or a co-culture of at least one of *Clostridium Ragsdalei, Clostridium autoethanogenum, Clostridium Coskatii*, and *Clostridium Ljungdahlii*.

* * * * *